United States Patent
Srinivasa Rao

(10) Patent No.: US 9,593,104 B2
(45) Date of Patent: Mar. 14, 2017

(54) PROCESS FOR THE PREPARATION OF OXAZOLIDINONE DERIVATIVES

(71) Applicant: Benova Labs Pvt Limited, Hyderabad (IN)

(72) Inventor: Kalleda Srinivasa Rao, Hyderabad (IN)

(73) Assignee: Benova Labs Pvt. Limited, Hyderabad (IN)

( * ) Notice: Subject to any disclaimer, the term of this patent is extended or adjusted under 35 U.S.C. 154(b) by 0 days.

(21) Appl. No.: 14/776,231

(22) PCT Filed: Mar. 11, 2014

(86) PCT No.: PCT/IB2014/059630
§ 371 (c)(1),
(2) Date: Sep. 14, 2015

(87) PCT Pub. No.: WO2014/141067
PCT Pub. Date: Sep. 18, 2014

(65) Prior Publication Data
US 2016/0039803 A1   Feb. 11, 2016

(30) Foreign Application Priority Data
Mar. 14, 2013 (IN) .......................... 1103/CHE/2013

(51) Int. Cl.
*C07D 263/20* (2006.01)
*C07D 209/48* (2006.01)
*C07D 263/24* (2006.01)
*C07D 413/06* (2006.01)

(52) U.S. Cl.
CPC ......... *C07D 413/06* (2013.01); *C07D 209/48* (2013.01); *C07D 263/20* (2013.01); *C07D 263/24* (2013.01)

(58) Field of Classification Search
None
See application file for complete search history.

(56) References Cited

U.S. PATENT DOCUMENTS 5,688,792 A    11/1997  Barbachyn et al.
7,429,661 B2 †  9/2008  Mohan Rao

FOREIGN PATENT DOCUMENTS

| WO | 99/24393 A1 † | 5/1999 |
| WO | 9924393 | 5/1999 |
| WO | 2005099353 | 10/2005 |
| WO | 2006008754 | 1/2006 |

OTHER PUBLICATIONS

International Search Report and Written Opinion for related PCT Application No. PCT/IB2014/059630 mailed Oct. 29, 2014 (6 pages).
Rajesh, T. et al. "A new and concise synthetic route to enantiopure Linezolid from (S)-epichlorohydrin", Der Pharma Chemica, 2011, vol. 3, Issue 5 (pp. 168-175).
Schaus, Scott E. et al. "Dynamic Kinetic Resolution of Epichlorohydrin via Enantioselective Catalytic Ring Opening with TMSN3. Practical Synthesis of Aryl Oxazolidinone Antibacterial Agents"; Tetrahedron Letters, 1996, vol. 37, No. 44 (pp. 7937-7940).
Scott E. Schaus, Dynamic Kinetic Resolution of Epichlorohydrin via Enantioselective Catalytic Ring Opening with TMSN3. Practical Synthesis of Aryl Oxazolidinone Antibacterial Agents, 4 pages, 1996, Elsevier.†

† cited by third party

*Primary Examiner* — Samantha Shterengarts
(74) *Attorney, Agent, or Firm* — Winthrop & Weinstine, P.A.

(57) ABSTRACT

The present invention relates to an improved process for the preparation of Oxazolidinone derivatives. More specifically, the present invention relates to an improved process for preparing (S)-N-[[3-[3-fluoro-4-[4-morpholinyl]phenyl]-2-oxo-5-oxazolidinyl]methyl]phthalimide, an intermediate used in the preparation of Oxazolidinone derivatives.

13 Claims, No Drawings

PROCESS FOR THE PREPARATION OF OXAZOLIDINONE DERIVATIVES

FIELD OF THE INVENTION

The present invention relates to an improved process for the preparation of Oxazolidinone derivatives. More specifically, the present invention relates to an improved process for preparing (S)-N-[[3-[3-fluoro-4-[4-morpholinyl]phenyl]-2-oxo-5-oxazolidinyl]methyl]phthalimide, an intermediate used in the preparation of Oxazolidinone derivatives.

BACKGROUND OF THE INVENTION

Oxazolidinones are a class of compounds containing 2-oxazolidone in the structure. Oxazolidinones are mainly used as antimicrobials. The antibacterial effect of oxazolidinones is by working as protein synthesis inhibitors, targeting an early step involving the binding of N-formylmethionyl-t-RNA to the ribosome.

Linezolid is the first synthetic oxazolidinone class of antibacterial agent and is chemically known as (S)-N-[[3-[3-fluoro-4-(4-morpholinyl)phenyl]-2-oxo-oxazolidin-5-yl]methyl]-acetamide and can be represented by the structure of general Formula I.

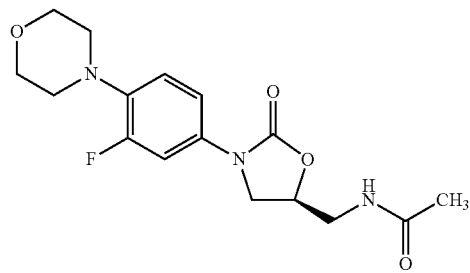

Linezolid is indicated in the treatment of infections caused by susceptible strains of the designated microorganisms such as Vancomycin-Resistant *Enterococcus faecium*, Nosocomial pneumonia, complicated skin and skin structure infection, uncomplicated skin and skin structure infections, community-acquired pneumonia and is commercially sold under the brand name Zyvox®.

Linezolid is first disclosed in U.S. Pat. No. 5,688,792. This patent also disclosed a process for the preparation of Linezolid, which is as depicted in scheme-I given below:

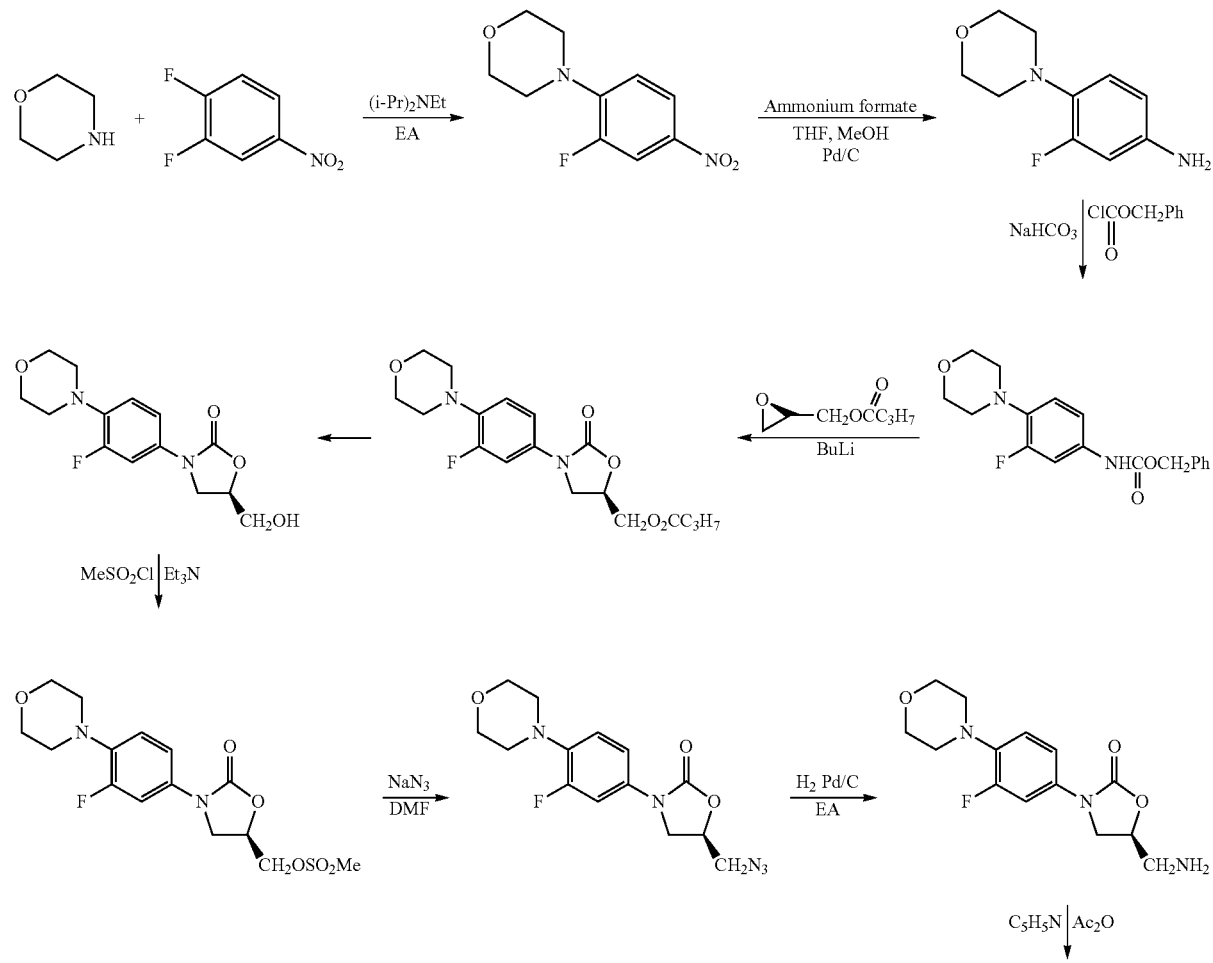

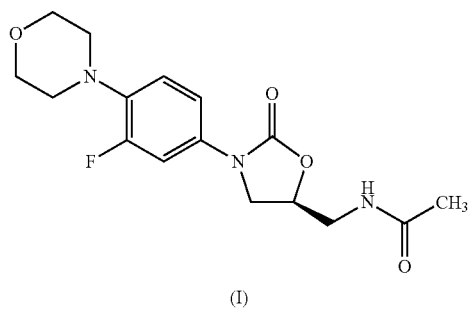

(I)

PCT Publication No. WO 1999/24393 A1 discloses a process for the preparation of oxazolidinone derivatives which is depicted in the scheme-II given below:

Scheme-II

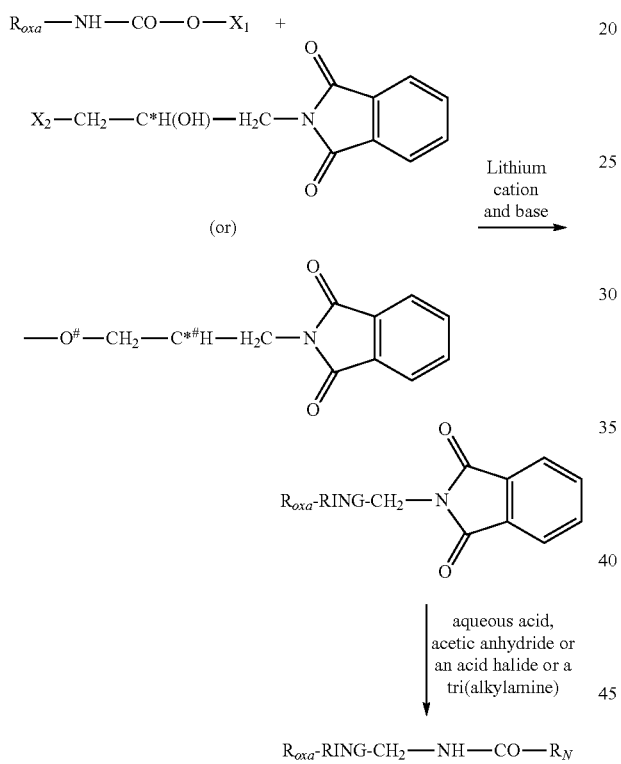

where $R_{oxa}$ is phenyl substituted with one fluoro and one substituted amino group, wherein the substituted amino groups include 4-(benzyloxycarbonyl)-1-piperazinyl, 4-morpholinyl and 4-hydroxyacetylpiperazinyl.

$X_1$ is $C_1$-$C_{20}$ alkyl;

$X_2$ is Cl, Br $R_N$ is $C_1$-$C_5$ alkyl # indicates that the atoms marked with (#) are bonded to each other resulting in the formation of ring and RING is

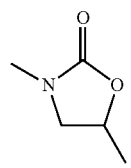

However, WO '393 does not disclose any specific examples or suitable conditions for the preparation of Linezolid and moreover, the use of lithium on commercial scale is not feasible.

PCT publication No. WO 2005/099353 A2 discloses a process for the preparation of Linezolid. The process is depicted in scheme-III given below:

Scheme-III

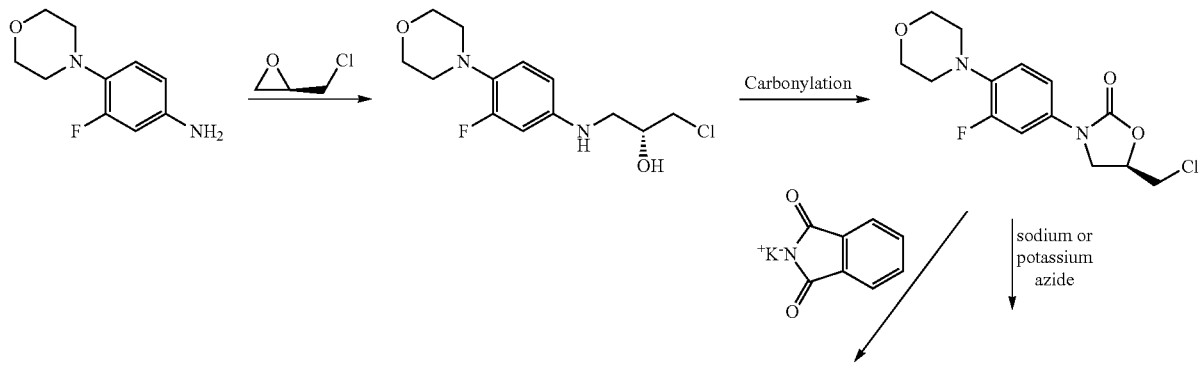

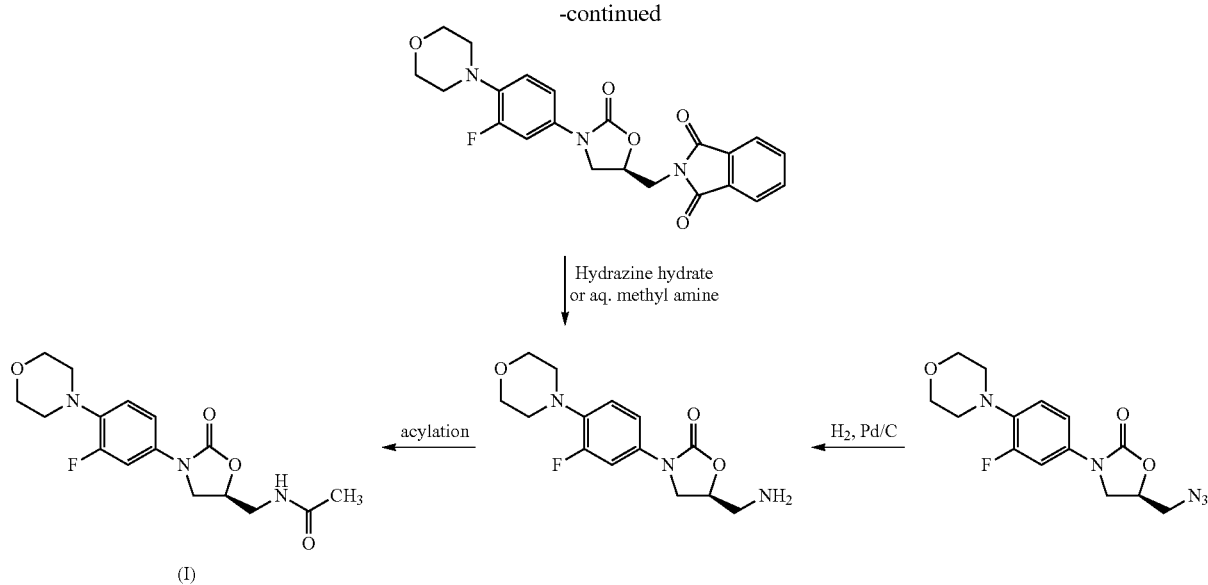
PCT publication No. WO 2006/008754 A1 discloses a process for the preparation of Linezolid. The process is depicted in scheme-IV given below:
Scheme-IV
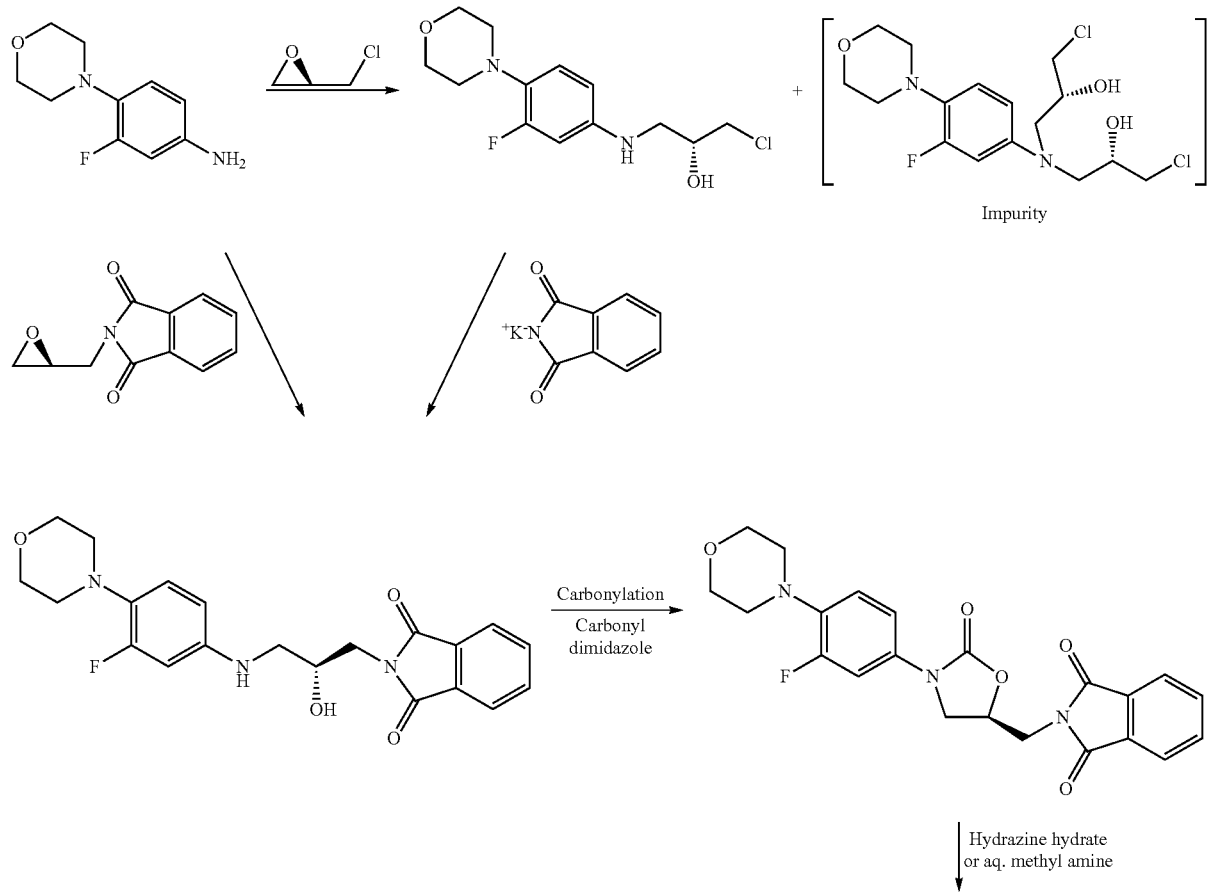

-continued

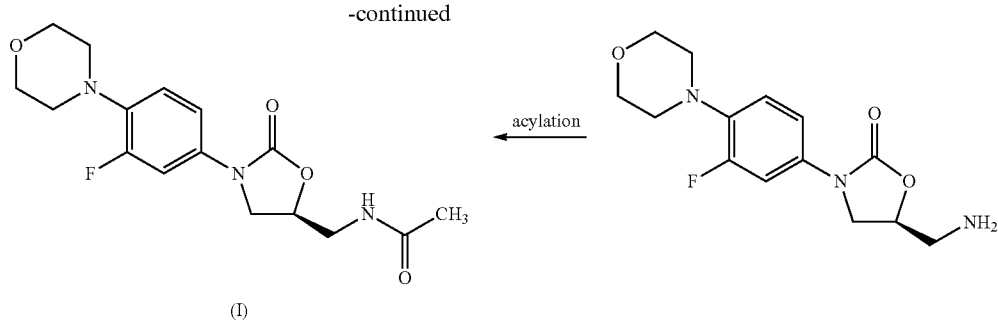

Condensation of 3-fluoro-4-morpholinyl aniline with epichlorohydrin may result in the formation of N,N-dialkylated compound as an impurity, which may be difficult to remove and effects the overall yield. Further, the process requires the use expensive reagents like carbonyl diimidazole during the carbonylation, which is hygroscopic and difficult in handling.

Thus there is a need in the art for an improved process for the preparation of Oxazolidinone derivatives, which employs less expensive, easily available and environment friendly reagents.

OBJECTIVE OF THE INVENTION

The main objective of the present invention is to provide cost-effective and commercially feasible process for the preparation of Oxazolidinone derivatives.

Another objective of the present invention is to provide a process for the preparation of Oxazolidinone derivatives which employs less expensive, easily available and environment friendly reagents.

SUMMARY OF THE INVENTION

Accordingly, the present invention provides an improved process for the preparation of (S)-N-[[3-[3-fluoro-4-[4-morpholinyl]phenyl]-2-oxo-5-oxazolidinyl]methyl]phthalimide of formula (II)

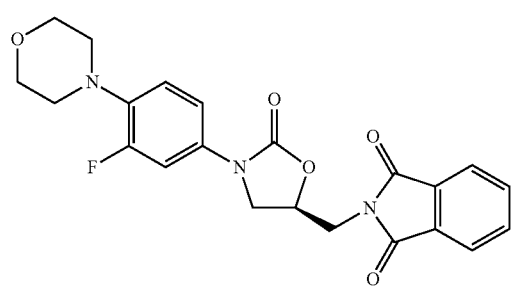

which comprises reacting carbamate compound of formula (III)

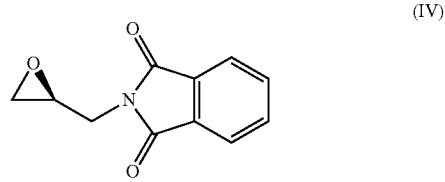

wherein X is O, NR', C(R")$_2$ and when X is O, NR', R represents hydrogen, C$_1$-C$_5$ alkyl, aryl, aralkyl; when X is C(R")$_2$, R represents hydrogen, halogen, C$_1$-C$_5$ alkyl, aryl, aralkyl;

R' represents hydrogen, C$_1$-C$_5$ alkyl, aryl, aralkyl or R' together with N and R forms an aryl, heteroaryl or heterocyclyl group;

R" represents hydrogen, C$_1$-C$_5$ alkyl, halogen;

with (S)-glycidyl phthalimide of formula (IV)

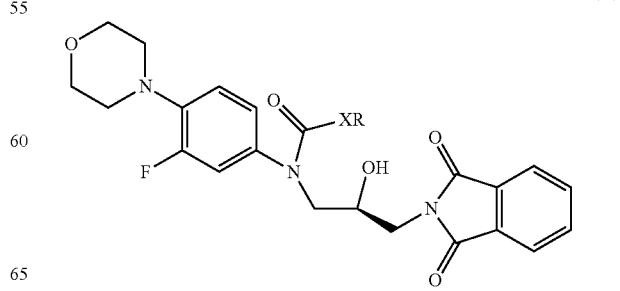

in the presence of a base or quaternary ammonium salt to yield compound of formula (II).

In another aspect, the present invention also provides novel intermediate of formula (V)

wherein X is O, NR', C(R")₂ and when X is O, NR', R represents hydrogen, C₁-C₅ alkyl, aryl, aralkyl; when X is C(R")₂, R represents hydrogen, halogen, C₁-C₅ alkyl, aryl, aralkyl;

R' represents hydrogen, C₁-C₅ alkyl, aryl, aralkyl or R' together with N and R forms an aryl, heteroaryl or heterocyclyl group;

R" represents hydrogen, C₁-C₅ alkyl, halogen;

DETAILED DESCRIPTION OF THE INVENTION

In an embodiment, the present invention provides an improved process for the preparation of (S)-N-[[3-[3-fluoro-4-[4-morpholinyl]phenyl]-2-oxo-5-oxazolidinyl]methyl] phthalimide of formula (II).

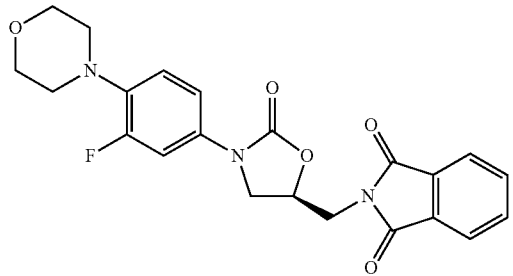

(II)

which comprises reacting carbamate compound of formula (III)

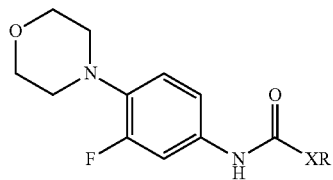

(III)

wherein X is O, NR', C(R")₂ and when X is O, NR', R represents hydrogen, C₁-C₅ alkyl, aryl, aralkyl; when X is C(R")₂, R represents hydrogen, halogen, C₁-C₅ alkyl, aryl, aralkyl;

R' represents hydrogen, C₁-C₅ alkyl, aryl, aralkyl or R' together with N and R forms an aryl, heteroaryl or heterocyclyl group;

R" represents hydrogen, C₁-C₅ alkyl, halogen;

with (S)-Glycidyl phthalimide of formula (IV)

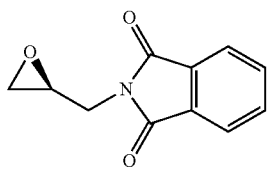

(IV)

using a base or quarternary ammonium salt and in the presence or absence of a solvent.

In another embodiment, the reaction is carried using a base or quaternary ammonium salt and in the presence or absence of a solvent at a temperature in the range of 50 to 150° C. The reaction is carried out for a period of 2 to 12 hours.

In accordance with the present invention, suitable aryl groups include phenyl, napthyl, indolyl, imidazolyl and the like; heteroaryl groups include pyrrolyl, furyl, thiophenyl, pyridyl, pyrimidinyl, quinolinyl, isoquinolinyl and the like; heterocyclyl group include morpholinyl, piperazinyl, piperidinyl, oxazolidinyl, quinolinyl, and the like.

Suitable base used according to the present invention is selected from organic base or inorganic base such as triethylamine, pyridine, dimethyl amino pyridine (DMAP), diethyl amino pyridine (DEAP), N-methyl morpholine, diisopropyl amine, diisopropylethylamine, potassium tert-butoxide, liquid ammonia, sodium hydroxide, potassium hydroxide, ammonium hydroxide, sodium carbonate, potassium carbonate, sodium bicarbonate, and the like. The amount of base used is less and is in the range of about 0.1 to 1.0 moles.

Suitable quarternary ammonium salts according to the present invention is selected such as tetrabutylammonium bromide (TBAB), tetrabutylammonium chloride (TBAC), tetraethylammonium bromide (TEAB), tetraethylammonium chloride (TEAC), triethylbenzylammonium bromide (TEBAB) and triethylbenzylammonium chloride (TEBAC), tetra-n-butylammonium fluoride, tetrabutylammonium hydroxide, tetrabutylammonium tribromide, tetraethylammonium chloride, tetraethylammonium iodide, tetramethylammonium chloride, tetramethylammonium hydroxide, tetramethylammonium pentafluoroxenate, and the like.

Suitable solvent used is selected from alcohols such as methanol, ethanol, isopropyl alcohol, and the like or mixture thereof; ketones, such as methyl isobutyl ketone, methyl ethyl ketone, n-butanone, and the like; halogenated solvents, such as dichloromethane, ethylene dichloride, chloroform, and the like; esters, such as ethyl acetate, n-propyl acetate, isopropyl acetate, and the like; hydrocarbon solvents, such as toluene, xylene, cyclohexane, and the like; ethers, such as 1,4-dioxane, tetrahydrofuran, and the like; and amides such as N,N-dimethylformamide, N,N-dimethylacetamide and the like or dimethylsulfoxide or mixture of solvents thereof.

In an embodiment, the present invention further involves conversion of compound of formula (II) to Linezolid of formula (I), which involves conversion of phthalimide compound of formula (II) to amine, followed by acylation to yield Linezolid using conventional methods known in the art.

The improved process for the preparation of formula II according to the present invention does not involve the use of lithium, lithium base or lithium salts.

In a preferred embodiment, the present invention provides an improved process for the preparation of (S)-N-[[3-[3-fluoro-4-[4-morpholinyl]phenyl]-2-oxo-5-oxazolidinyl] methyl]phthalimide of formula (II),

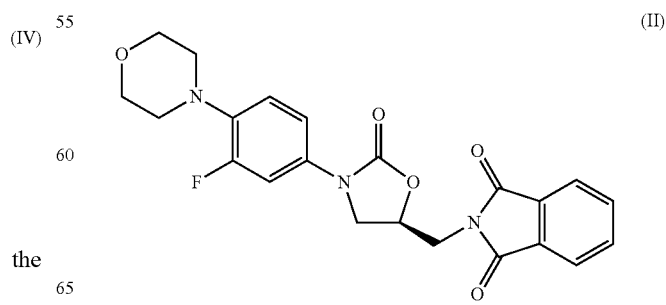

(II)

which comprises reacting carbamate compound of formula (III)

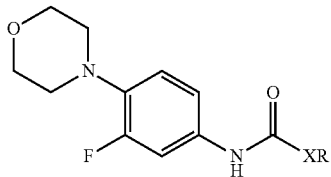
(III)

wherein X is O, NR', C(R")₂ and when X is O, NR', R represents hydrogen, C₁-C₅ alkyl, aryl, aralkyl; when X is C(R")₂, R represents hydrogen, halogen, C₁-C₅ alkyl, aryl, aralkyl;
R' represents hydrogen, C₁-C₅ alkyl, aryl, aralkyl or R' together with N and R forms an aryl, heteroaryl or heterocyclyl group;
R" represents hydrogen, C₁-C₅ alkyl, halogen;
with (S)-Glycidyl phthalimide of formula (IV)

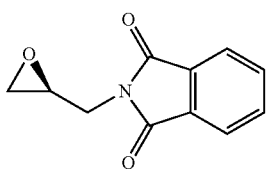
(IV)

using a base selected from organic base or inorganic base or quaternary ammonium salts at a temperature in the range of 50 to 150° C. in the presence or absence of solvents such as alcohols, ketones, halogenated solvents, esters, hydrocarbon solvents, ethers, amides and the like or mixture thereof.

In yet another embodiment, the process for the preparation of (S)-N-[[3-[3-fluoro-4-[4-morpholinyl]phenyl]-2-oxo-5-oxazolidinyl]methyl]phthalimide of formula (II) involves the formation of novel compound of formula (V),

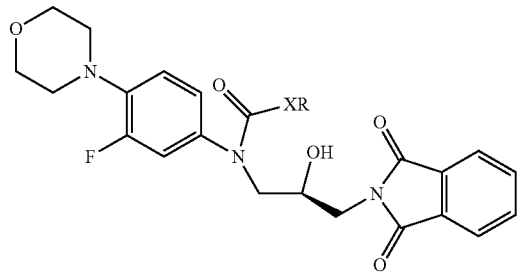
(V)

wherein X is O, NR', C(R")₂ and when X is O, NR', R represents hydrogen, C₁-C₅ alkyl, aryl, aralkyl; when X is C(R")₂, R represents hydrogen, halogen, C₁-C₅ alkyl, aryl, aralkyl;
R' represents hydrogen, C₁-C₅ alkyl, aryl, aralkyl or R' together with N and R forms an aryl, heteroaryl or heterocyclyl group;
R" represents hydrogen, C₁-C₅ alkyl, halogen;
which may be optionally isolated.

In yet another embodiment, the present invention provides novel compound of formula (V).

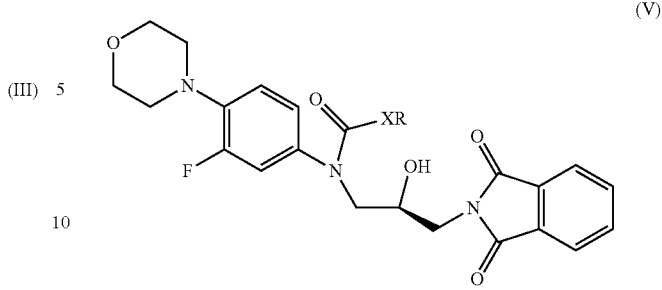
(V)

wherein X is O, NR', C(R")₂ and when X is O, NR', R represents hydrogen, C₁-C₅ alkyl, aryl, aralkyl; when X is C(R")₂, R represents hydrogen, halogen, C₁-C₅ alkyl, aryl, aralkyl;
R' represents hydrogen, C₁-C₅ alkyl, aryl, aralkyl or R' together with N and R forms an aryl, heteroaryl or heterocyclyl group;
R" represents hydrogen, C₁-C₅ alkyl, halogen;
The preferred compounds of formula (V) according to the present invention is selected from
[ethyl-N-[3-phthalimido-(2R)-hydroxypropyl]-N-3-fluoro-4-[4-morpholinyl]]phenylcarbamate,
[methyl-N-[3-phthalimido-(2R)-hydroxypropyl]-N-3-fluoro-4-[4-morpholinyl]]phenylcarbamate,
[propyl-N-[3-phthalimido-(2R)-hydroxypropyl]-N-3-fluoro-4-[4-morpholinyl]]phenylcarbamate and the like.
[isopropyl-N-[3-phthalimido-(2R)-hydroxypropyl]-N-3-fluoro-4-[4-morpholinyl]]phenylcarbamate and the like.

In yet another embodiment, the present invention provides a process for the preparation of Linezolid of formula (I) which comprises:
i) reacting carbamate compound of formula (III)

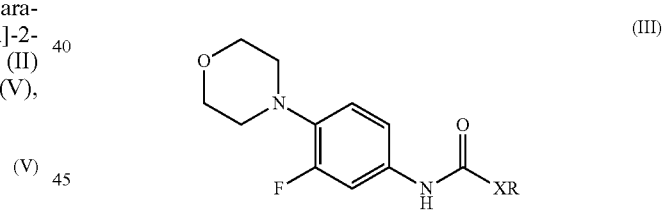
(III)

wherein X is O, NR', C(R")₂ and when X is O, NR', R represents hydrogen, C₁-C₅ alkyl, aryl, aralkyl; when X is C(R")₂, R represents hydrogen, halogen, C₁-C₅ alkyl, aryl, aralkyl;
R' represents hydrogen, C₁-C₅ alkyl, aryl, aralkyl or R' together with N and R forms an aryl, heteroaryl or heterocyclyl group;
R" represents hydrogen, C₁-C₅ alkyl, halogen;
with (S)-glycidyl phthalimide of formula (IV)

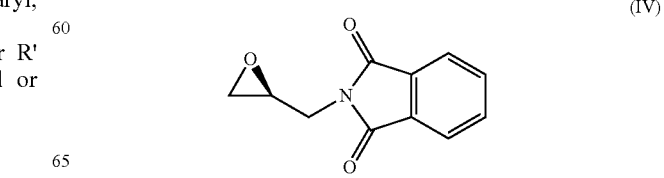
(IV)

using a base or quaternary ammonium salt and in the presence or absence of a solvent to produce (S)-N-[[3-[3-fluoro-4-[4-morpholinyl]phenyl]-2-oxo-oxazolidin-5-yl]methyl]phthalimide of formula (II),

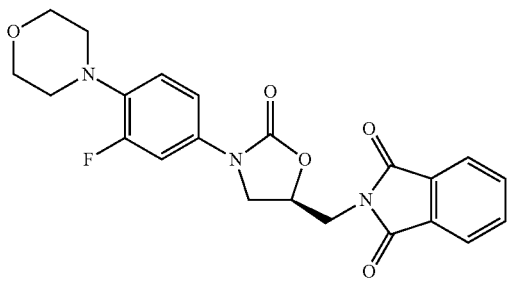
(II)

ii) converting the compound of formula (II) to amine and followed by acetylation to yield Linezolid of formula (I), and
iii) isolating the Linezolid in pure form.

In another preferred embodiment, the present invention provides an improved process for the preparation of (S)-N-[[3-[3-fluoro-4-[4-morpholinyl]phenyl]-2-oxo-5-oxazolidinyl]methyl]phthalimide of formula (II)

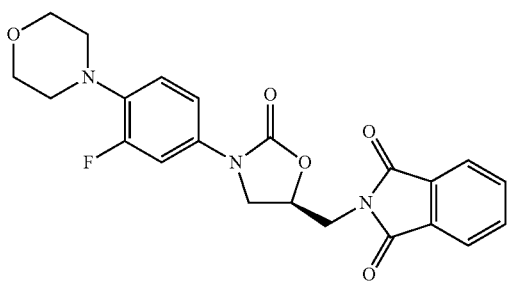
(II)

which comprises reacting N-ethoxycarbonyl-3-fluoro-4-morpholinyl aniline of formula (IIIa)

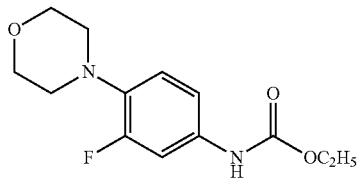
(IIIa)

with (S)-Glycidyl phthalimide of formula (IV)

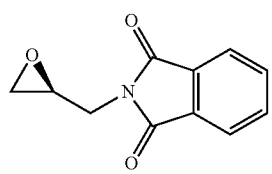
(IV)

using a base selected from organic base or inorganic base or quaternary ammonium salt and in the presence or absence of a solvent at a temperature of 50-150° C. for about 2-12 hours.

In another preferred embodiment, the present invention provides a process for the preparation of Linezolid of formula (I) which comprises:

i) reacting N-ethoxycarbonyl 3-fluoro-4-morpholinyl aniline of formula (Ma)

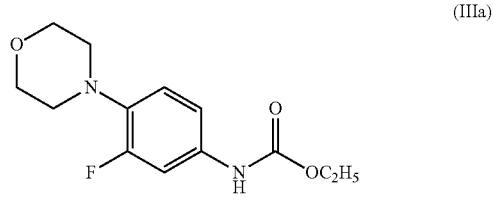 [SMILES: CCOC(=O)Nc1ccc(N2CCOCC2)c(F)c1]
(IIIa)

with (S)-Glycidyl phthalimide of formula (IV)

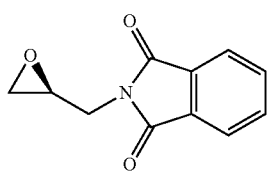
(IV)

using a base selected from organic base or inorganic base or quaternary ammonium salt and in the presence or absence of a solvent at a temperature of 50-150° C. to produce (S)-N-[[3-[3-fluoro-4-[4-morpholinyl]phenyl]-2-oxo-oxazolidin-5-yl]methyl]phthalimide of formula (II),

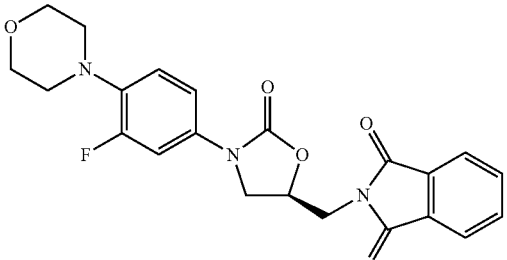
(II)

ii) converting the compound of formula (II) to amine and followed by acetylation to yield Linezolid of formula (I), and
iii) isolating the Linezolid in pure form.

The reaction process for the preparation of Linezolid according to the present invention is shown in scheme-V given below:

Scheme-V

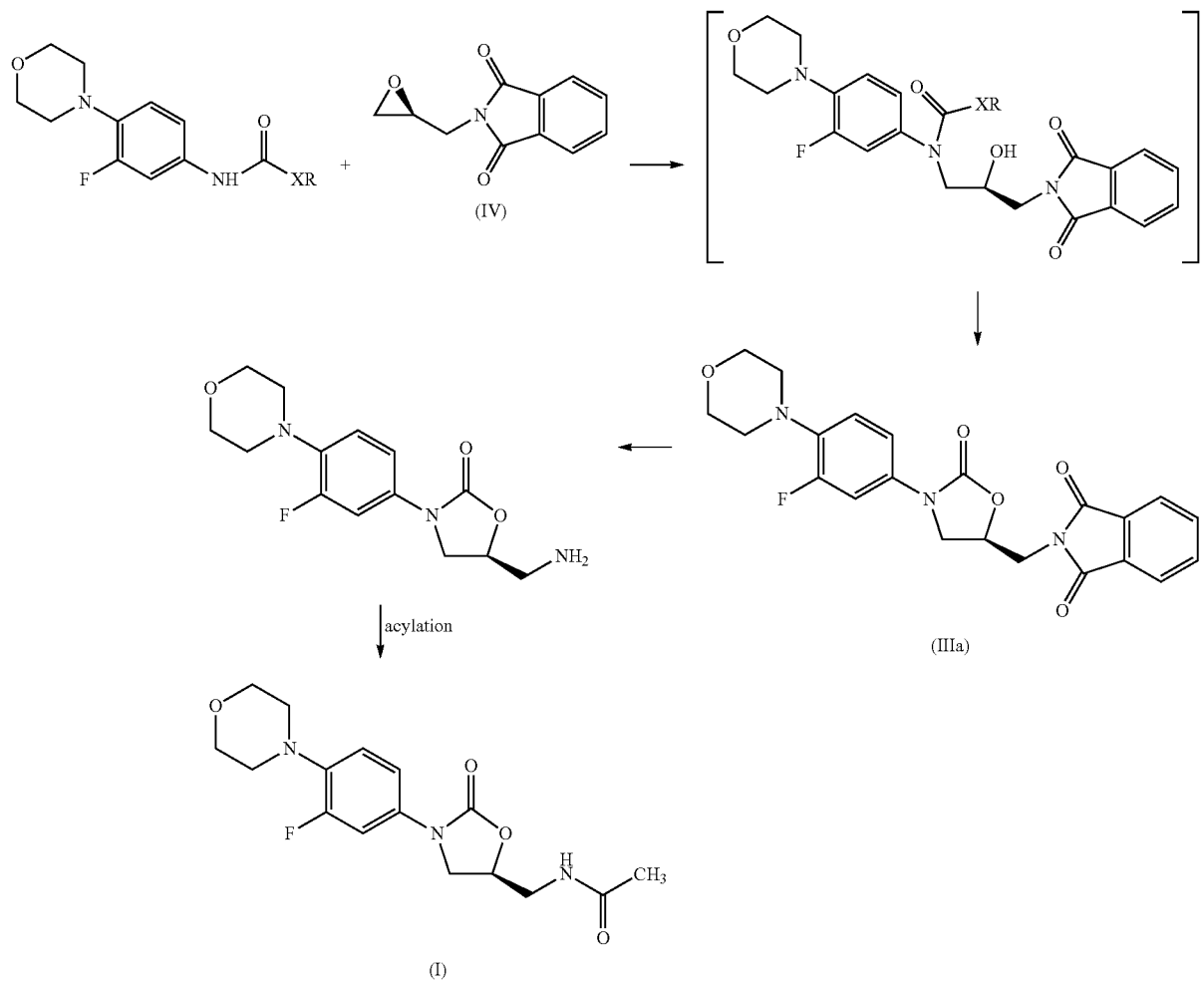

wherein X is O, NR', C(R")$_2$ and when X is O, NR', R represents hydrogen, C$_1$-C$_5$ alkyl, aryl, aralkyl; when X is C(R")$_2$, R represents hydrogen, halogen, C$_1$-C$_5$ alkyl, aryl, aralkyl;

R' represents hydrogen, C$_1$-C$_5$ alkyl, aryl, aralkyl or R' together with N and R forms an aryl, heteroaryl or heterocyclyl group;

R" represents hydrogen, C$_1$-C$_5$ alkyl, halogen;

The conversion of phthalimide compound of formula (II) to amine and followed by acylation to yield Linezolid of formula (I) can be carried out using conventional methods known in the art.

Linezolid produced according to the present invention may be in the form of amorphous or crystalline form.

Advantages of the Present Invention:
1. The process of the present invention is simple, safe, environmental friendly and involves less expensive reagents.
2. The process involves use of less amount such as 0.1 to 0.2 moles of base,
3. The process is commercially viable and results the compounds in high yield, which makes the process cost effective.

While the present invention has been described in terms of its specific embodiments, certain modifications and equivalents will be apparent to those skilled in the art and are intended to be included within the scope of the present invention. The invention is illustrated below with reference to inventive and comparative examples and should not be construed to limit the scope of the invention.

Preparation 1

Preparation of N-ethoxycarbonyl 3-fluoro-4-morpholinyl aniline

To a mixture of 3-fluoro-4-morpholinyl aniline (50 g) and methylene dichloride (500 ml) was added N,N-diisopropyl ethylamine (41.5 g) and stirred the reaction mixture for about 5 min. Cooled the reaction mixture to 0-5° C. and ethylchloroformate (30.5 g) was added drop wise. The temperature of the reaction mass was raised to 25-30° C. and maintained at the same temperature for about 30 min. Water (200 ml) was added to the reaction mass after the TLC was passed and stirred the reaction mass for about 15 min. Filtered the obtained solid and dried to get (41 g) title compound.

Example 1

Preparation of (S)-N-[[3-[3-fluoro-4-[4-morpholinyl]phenyl]-2-oxo-5-oxazolidinyl]methyl]phthalimide Mixture of N-ethoxycarbonyl 3-fluoro-4-morpholinyl aniline (30 g), (S)-Glycidyl phthalimide (27 g) and triethylamine (1.5 ml) were heated to 90-95° C. and maintained at the same temperature for about 6 hours. The reaction mass was cooled to ambient temperature and acetone (240 ml) was added. Heated the reaction mass to reflux temperature and stirred for about 30 minutes. The reaction mass was cooled to ambient temperature, filtered the solid obtained, washed the cake with acetone (120 ml) and dried to get (40 g) the title compound.

Example 2

Preparation of (S)-N-[[3-[3-fluoro-4-[4-morpholinyl]phenyl]-2-oxo-5-oxazolidinyl]methyl]phthalimide Mixture of N-ethoxycarbonyl 3-fluoro-4-morpholinyl aniline (30 g), (S)-Glycidyl phthalimide (27 g) and N,N-diisopropylethylamine (1.5 ml) were heated to 90-95° C. and maintained at the same temperature for about 6 hours. The reaction mass was cooled to ambient temperature and acetone (240 ml) was added. Heated the reaction mass to reflux temperature and stirred for about 30 minutes. The reaction mass was cooled to ambient temperature, filtered the solid obtained, washed the cake with acetone (120 ml) and dried to get (35.6 g) the title compound.

Example 3

Preparation of (S)-N-[[3-[3-fluoro-4-[4-morpholinyl]phenyl]-2-oxo-5-oxazolidinyl]methyl]phthalimide Mixture of N-ethoxycarbonyl 3-fluoro-4-morpholinyl aniline (5 g), (S)-Glycidyl phthalimide (4.5 g), N,N-Dimethyl formamide (5 ml) and triethylamine (0.25 ml) were heated to reflux temperature and maintained at the same temperature for about 11 hours. The reaction mass was cooled to ambient temperature, acetone (40 ml) was added and stirred for about 30 minutes. Filtered the solid obtained, washed the cake with acetone (20 ml) and dried to get (3.6 g) the title compound.

Example 4

Preparation of (S)-N-[[3-[3-fluoro-4-[4-morpholinyl]phenyl]-2-oxo-5-oxazolidinyl]methyl]phthalimide Mixture of N-ethoxycarbonyl 3-fluoro-4-morpholinyl aniline (5 g), (S)-Glycidyl phthalimide (4.5 g) and tetrabutylammoniumbromide (1 g) were heated to 90-95° C. and maintained at the same temperature for about 4 hours. The temperature of the reaction mass was raised to 110-115° C. and maintained at the same temperature for about 2 hours. Cooled the reaction mass to 50° C. and acetone (40 ml) was added. Heated the reaction mass to reflux temperature and stirred for about 30 minutes. The reaction mass was cooled to ambient temperature, filtered the solid obtained, washed the cake with acetone (10 ml) and dried to get (3.8 g) the title compound.

Example 5

Preparation of (S)-N-[[3-[3-fluoro-4-[4-morpholinyl]phenyl]-2-oxo-5-oxazolidinyl]methyl]phthalimide Mixture of N-ethoxycarbonyl 3-fluoro-4-morpholinyl aniline (5 g), (S)-Glycidyl phthalimide (4.5 g) and triethylbenzylammoniumchloride (1 g) were heated to 90-95° C. and maintained at the same temperature for about 6 hours. Cooled the reaction mass to 50° C. and acetone (40 ml) was added. Heated the reaction mass to reflux temperature and stirred for about 30 minutes. The reaction mass was cooled to ambient temperature, filtered the solid obtained, washed the cake with acetone (10 ml) and dried to get (6.1 g) the title compound.

Example 6

Preparation of Ethyl N-[3-phthalimido-(2R)-hydroxypropyl]-N-3-fluoro-4-(4-morpholinyl) phenyl carbamate Mixture of N-ethoxycarbonyl 3-fluoro-4-morpholinyl aniline (5 g), (S)-Glycidyl phthalimide (4.5 g) and triethyl amine (0.25 ml) were heated to 90-95° C. and maintained at the same temperature for about 1 hour. The reaction mass was cooled to ambient temperature and chromatographed on silica gel eluting with ethyl acetate and n-hexane. The combined fractions gave white solid, which was triturated with n-hexane to get (2.5 g) of title compound characterized by m.p=113.8-115.6° C.; HPLC purity=98.4%. Mass: (M+1) 472.2; and $^1$H NMR: (400 MHz, DMSO-D6), δ 1.1 (t, 3H), 3.0 (t, 4H), 3.4 (m, 1H), 3.5 (q, 2H), 3.7 (m, 5H), 4.0 (t, 4H), 6.95-7.0 (t, 1H), 7.1 (d, 1H), 7.15-7.2 (dd, 1H), 7.8-7.9 (m, 4 H).

Example-7

Preparation of (S)-N-[ [3-[3-fluoro-4-(4-morpholinyl)phenyl]-2-oxo-oxazolidin-5-yl]methyl]-acetamide (Linezolid)

Mixture of methanol (80 ml) and hydrazine hydrate (13 g) were added to a flask containing (S)-N-[[3-[3-fluoro-4-[4-morpholinyl]phenyl]-2-oxo-5-oxazolidinyl]methyl]phthalimide (20 g), heated to reflux temperature and maintained at the same temperature for about 1 hour. Cooled the reaction mass to ambient temperature, water (80 ml) was added and extracted with methylene dichloride (240 ml). The combined extractions were washed with water (160 ml) and separated the organic layer. Triethyl amine (10 g) was added to the organic layer, cooled the reaction mixture to 10-15° C. and acetic anhydride (10 g) was added. The temperature of the reaction mass was raised to 25-30° C. and maintained at the same temperature for about 1 hour. The solvent was distilled off completely and ethyl acetate (100 ml) was added, filtered the obtained solid and dried to get (9 g) the title compound as white solid.

melting point=181.5-182.5° C.; HPLC purity=99.6%.

I claim:

1. An improved process for the preparation of (S)-N-[[3-[3-fluoro-4-[4-morpholinyl]phenyl]-2-oxo-5-oxazolidinyl]methyl]phthalimide of formula (II),

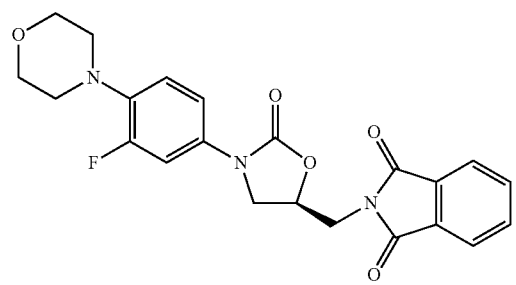
(II)

which comprises reacting carbamate compound of formula (III)

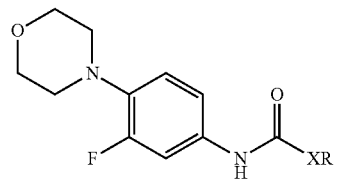
(III)

wherein X is O, NR', or $C(R'')_2$ and when X is O or NR', R represents hydrogen, $C_1$-$C_5$ alkyl, aryl, or aralkyl; when X is $C(R'')_2$, R represents hydrogen, halogen, $C_1$-$C_5$ alkyl, aryl, or aralkyl;

R' represents hydrogen, $C_1$-$C_5$ alkyl, aryl, aralkyl or R' together with N and R forms an aryl, heteroaryl or heterocyclyl group;

R" represents hydrogen, $C_1$-$C_5$ alkyl or halogen;

with (S)-glycidyl phthalimide of formula (IV)

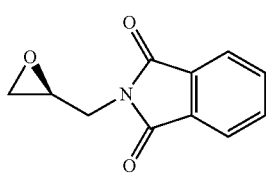
(IV)

using a base or quaternary ammonium salt and in the presence or absence of a solvent.

2. An improved process for the preparation of (S)-N-[[3-[3-fluoro-4-[4-morpholinyl]phenyl]-2-oxo-5-oxazolidinyl]methyl]phthalimide of formula (II),

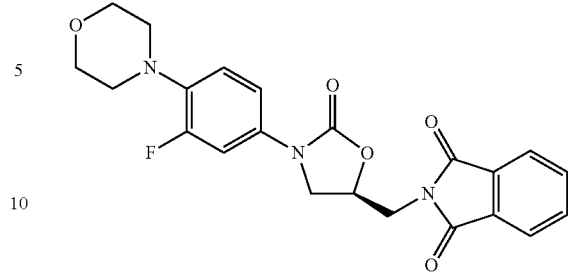
(II)

as claimed in claim 1 which comprises reacting N-ethoxycarbonyl-3-fluoro-4-morpholinyl aniline of formula (IIIa)

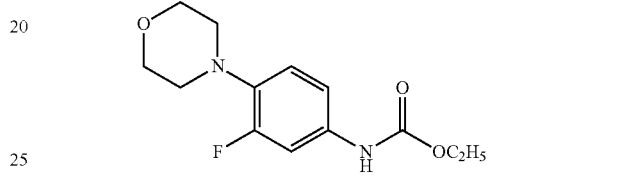
(IIIa)

with (S)-glycidyl phthalimide of formula (IV)

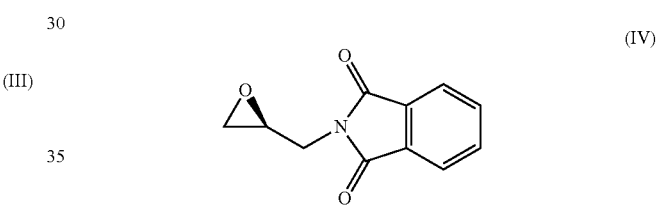
(IV)

using a base or quaternary ammonium salt and in the presence or absence of a solvent.

3. The process as claimed in claim 1, wherein the said base is selected from triethylamine, pyridine, dimethyl amino pyridine (DMAP), diethyl amino pyridine (DEAP), N-methyl Morpholine, diisopropyl amine, diisopropylethylamine, potassium tert-butoxide, sodium hydroxide, potassium hydroxide, ammonium hydroxide, liquid ammonia, sodium carbonate, potassium carbonate and sodium bicarbonate.

4. The process as claimed in claim 1 wherein the quaternary ammonium salt is selected from tetrabutylammonium bromide (TBAB), tetrabutylammonium chloride (TBAC), tetraethylammonium bromide (TEAB), tetraethylammonium chloride (TEAC), triethylbenzylammonium bromide (TEBAB) and triethylbenzylammonium chloride (TEBAC), tetra-n-butylammonium fluoride, tetrabutylammonium hydroxide, tetrabutylammonium tribromide, tetraethylammonium chloride, tetraethylammonium iodide, tetramethylammonium chloride, tetramethylammonium hydroxide, and tetramethylammonium pentafluoroxenate.

5. The process as claimed in claim 1, wherein the solvent is selected from alcohols, ketones, halogenated solvents, esters, hydrocarbon solvents, ethers, amides and dimethylsulfoxide.

6. The process for the preparation of (S)-N-[[3-[3-fluoro-4-[4-morpholinyl]phenyl]-2-oxo-5-oxazolidinyl]methyl]phthalimide of formula (II) as claimed in claim 1, involves the formation of novel compound of formula (V)

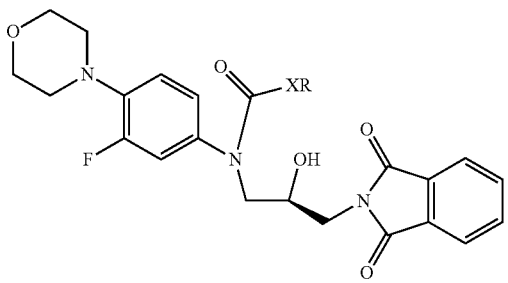

(V)

wherein X is O, NR', or C(R")$_2$ and when X is O or NR', R represents hydrogen, C$_1$-C$_5$ alkyl, aryl, or aralkyl; when X is C(R")$_2$, R represents hydrogen, halogen, C$_1$-C$_5$ alkyl, aryl, or aralkyl;

R' represents hydrogen, C$_1$-C$_5$ alkyl, aryl, aralkyl or R' together with N and R forms an aryl, heteroaryl or heterocyclyl group;

R" represents hydrogen, C$_1$-C$_5$ alkyl, or halogen;

which is optionally isolated.

7. Novel compound of formula (V)

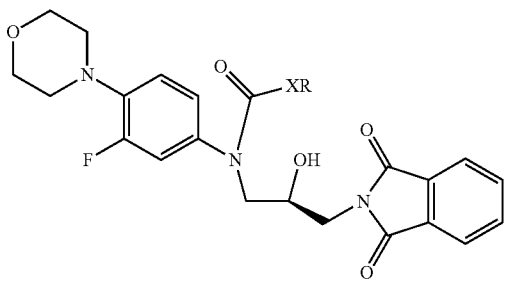

(V)

wherein X is O, NR', or C(R")$_2$ and when X is O or NR', R represents hydrogen, C$_1$-C$_5$ alkyl, aryl, or aralkyl; when X is C(R")$_2$, R represents hydrogen, halogen, C$_1$-C$_5$ alkyl, aryl, or aralkyl;

R' represents hydrogen, C$_1$-C$_5$ alkyl, aryl, aralkyl or R' together with N and R forms an aryl, heteroaryl or heterocyclyl group;

R" represents hydrogen, C$_1$-C$_5$ alkyl, or halogen.

8. The compound according to claim 7, is selected from

[ethyl-N-[3-phthalimido-(2R)-hydroxypropyl]-N-3-fluoro-4-[4-morpholinyl]]phenylcarbamate,

[methyl-N[3-phthalimido-(2R)-hydroxypropyl]-N-3-fluoro-4-[4morpholinyl]]phenylcarbamate,

[propyl-N-[3-phthalimido-(2R)-hydroxypropyl]-N-3-fluoro-4-[4-morpholinyl]]phenylcarbamate, and

[isopropyl-N-[3-phthalimido-(2R)-hydroxypropyl]-N-3-fluoro-4-[4-morpholinyl]]phenylcarbamate.

9. A process for the preparation of Linezolid of formula (I)

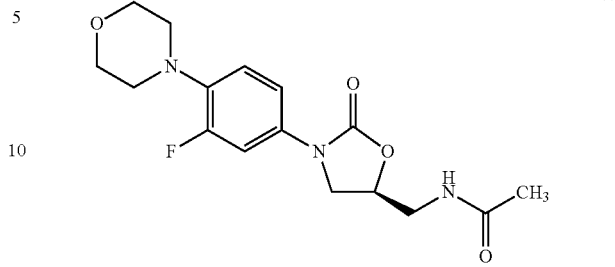

(I)

which comprises converting the compound of formula (II) prepared according to claim 1.

10. The process as claimed in claim 2, wherein the said base is selected from triethylamine, pyridine, dimethyl amino pyridine (DMAP), diethyl amino pyridine (DEAP), N-methyl Morpholine, diisopropyl amine, diisopropylethylamine, potassium tert-butoxide, sodium hydroxide, potassium hydroxide, ammonium hydroxide, liquid ammonia, sodium carbonate, potassium carbonate and sodium bicarbonate.

11. The process as claimed in claim 2 wherein the quaternary ammonium salt is selected from tetrabutylammonium bromide (TBAB), tetrabutylammonium chloride (TBAC), tetraethylammonium bromide (TEAB), tetraethylammonium chloride (TEAC), triethylbenzylammonium bromide (TEBAB) and triethylbenzylammonium chloride (TEBAC), tetra-n-butylammonium fluoride, tetrabutylammonium hydroxide, tetrabutylammonium tribromide, tetraethylammonium chloride, tetraethylammonium iodide, tetramethylammonium chloride, tetramethylammonium hydroxide, and tetramethylammonium pentafluoroxenate.

12. The process as claimed in claim 2, wherein the solvent is selected from alcohols, ketones, halogenated solvents, esters, hydrocarbon solvents, ethers, amides and dimethylsulfoxide.

13. A process for the preparation of Linezolid of formula (I)

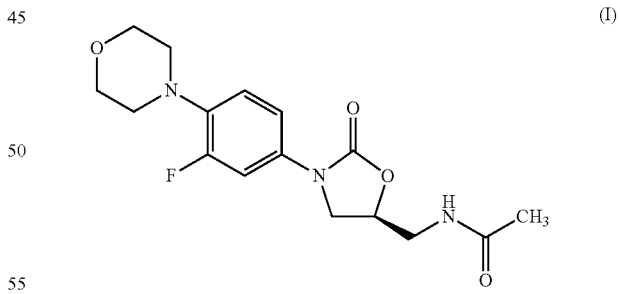

(I)

which comprises converting the compound of formula (II) prepared according to claim 2.

* * * * *